(12) United States Patent
Narkhede

(10) Patent No.: US 11,826,091 B2
(45) Date of Patent: Nov. 28, 2023

(54) BIPOLAR ELECTROSURGICAL CUTTING AND COAGULATION INSTRUMENT

(71) Applicant: XCELLANCE MEDICAL TECHNOLOGIES PVT LTD, Navi Mumbai (IN)

(72) Inventor: Pradip Barsu Narkhede, Rabale (IN)

(73) Assignee: XCELLANXE MEDICAL TECHNOLOGIES PVT LTD

( * ) Notice: Subject to any disclaimer, the term of this patent is extended or adjusted under 35 U.S.C. 154(b) by 562 days.

(21) Appl. No.: 16/323,815

(22) PCT Filed: Aug. 10, 2017

(86) PCT No.: PCT/IN2017/000112
§ 371 (c)(1),
(2) Date: Feb. 7, 2019

(87) PCT Pub. No.: WO2018/033931
PCT Pub. Date: Feb. 22, 2018

(65) Prior Publication Data
US 2019/0175253 A1      Jun. 13, 2019

(30) Foreign Application Priority Data
Aug. 16, 2016   (IN) .............................. 201621027806

(51) Int. Cl.
*A61B 18/14*      (2006.01)
*A61B 18/00*      (2006.01)

(52) U.S. Cl.
CPC .. *A61B 18/148* (2013.01); *A61B 2018/00589* (2013.01); *A61B 2018/00601* (2013.01); *A61B 2018/00607* (2013.01); *A61B 2018/00928* (2013.01); *A61B 2018/00958* (2013.01); *A61B 2018/1412* (2013.01); *A61B 2018/1425* (2013.01)

(58) Field of Classification Search
CPC ........ A61B 18/148; A61B 2018/00589; A61B 2018/1412; A61B 2018/1425; A61B 2018/00601; A61B 2018/00607
See application file for complete search history.

(56) References Cited

U.S. PATENT DOCUMENTS

| | | | | |
|---|---|---|---|---|
| 4,202,337 | A | * | 5/1980 | Hren .................. A61B 18/1402 606/50 |
| 5,281,216 | A | | 1/1994 | Klicek |
| 6,241,724 | B1 | * | 6/2001 | Fleischman ........ A61B 18/1492 600/374 |

(Continued)

*Primary Examiner* — Joseph A Stoklosa
*Assistant Examiner* — Annie L Shoulders
(74) *Attorney, Agent, or Firm* — Taft Stettinius & Hollister LLP; Derek B. Lavender

(57) ABSTRACT

A bipolar surgical instrument having a front region (3) with at least four coagulation elements (6, 7, 8, 9) entered in the slots at the at least four corners of a rectangle or at least four quarters of a circle of the insulation body (22) for coagulating and one cutting element at the centre of insulating body for cutting the tissue and/or vessel in the body, thereby having an at least five electrode arrangement for handling and treating the tissue and/or vessel. The cutting element (10) can be at least one blade or at least one needle and it can be fixed or moved longitudinally in an advanced position or retracted position.

11 Claims, 15 Drawing Sheets

(56) References Cited

U.S. PATENT DOCUMENTS

| | | | | |
|---|---|---|---|---|
| 6,494,881 B1* | 12/2002 | Bales | | A61B 18/149 |
| | | | | 606/41 |
| 2003/0181904 A1* | 9/2003 | Levine | | A61B 18/1402 |
| | | | | 606/45 |
| 2008/0103494 A1* | 5/2008 | Rioux | | A61B 18/1482 |
| | | | | 606/37 |
| 2009/0171352 A1* | 7/2009 | Sutter | | A61B 18/1402 |
| | | | | 606/49 |
| 2013/0085497 A1* | 4/2013 | Chang | | A61B 17/32 |
| | | | | 606/45 |
| 2014/0276797 A1* | 9/2014 | Batchelor | | A61B 18/1233 |
| | | | | 606/42 |
| 2015/0320491 A1* | 11/2015 | Hörlle | | A61B 18/1485 |
| | | | | 606/48 |
| 2016/0008052 A1 | 1/2016 | Scheller | | |
| 2017/0049505 A1* | 2/2017 | Weiler | | A61B 18/1445 |
| 2017/0086915 A1* | 3/2017 | Batchelor | | A61B 18/1206 |

* cited by examiner

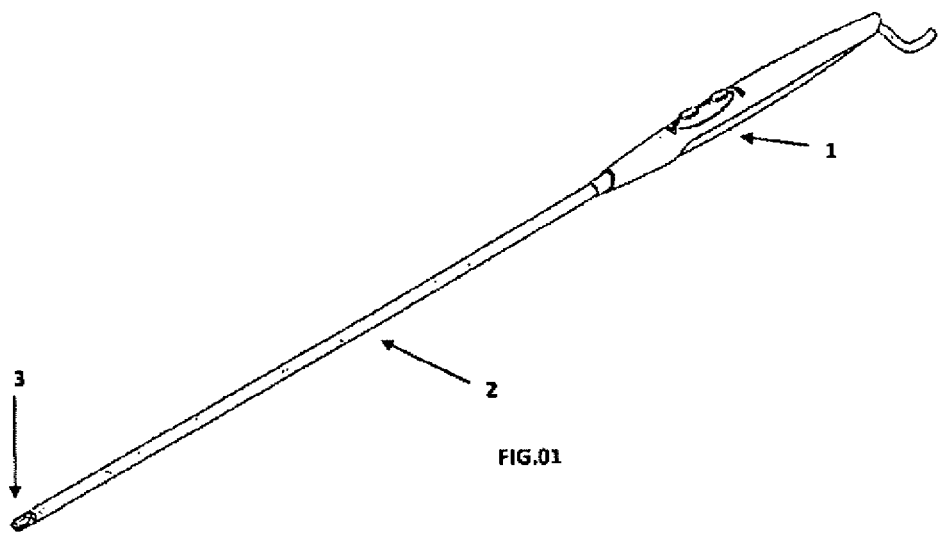
FIG.01
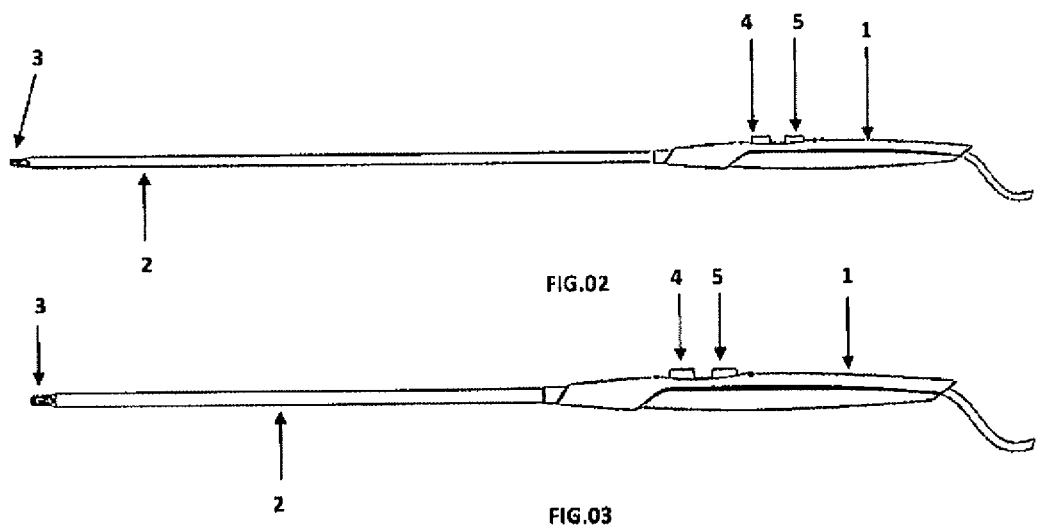
FIG.02
FIG.03

DETAIL A

FIG.18
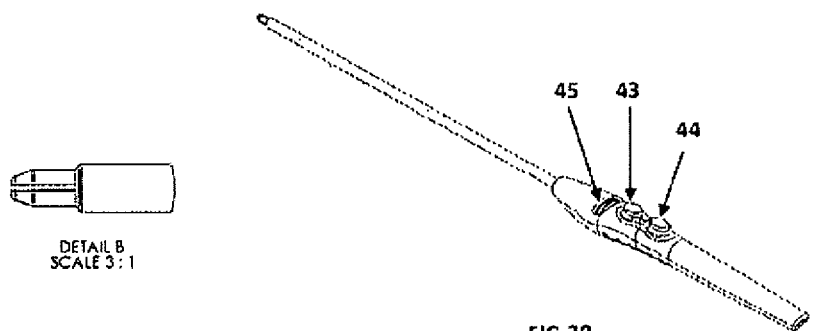
DETAIL B
SCALE 3:1
FIG.19
FIG.20

SECTION A-A

BIPOLAR ELECTROSURGICAL CUTTING AND COAGULATION INSTRUMENT

FIELD OF THE INVENTION

The present invention relates, in general to a surgical instrument and more particularly, to a bipolar surgical instrument having a front region with at least four coagulation elements entered in the slots at the at least four corners of a rectangle or at least four quarters of a circle of the insulation body for coagulating and one cutting element at the centre of insulating body for cutting the tissue and/or vessel in the body, thereby having at least five electrode arrangement for handling and treating the tissue and or vessel.

BACKGROUND OF THE INVENTION

Electro surgery involves application of high frequency electrical current to a surgical site to cut, ablate, coagulate, cauterize, desiccate or seal tissue. Bipolar coagulation is a technique for achieving occlusion of blood vessels and tissue bundles by application of high frequency electrical current.

Tissue or vessel sealing is a process of liquefying the collagen, elastin and ground substances in the tissue so that they reform into a fused mass with significantly-reduced demarcation between the opposing tissue structures. Generally, the electrical configuration of electrosurgical devices can be categorized in two classifications: 1) monopolar electrosurgical device; and 2) bipolar electrosurgical device.

In monopolar electrosurgical forceps the active electrode is placed in the target site and can be used to cut tissue and coagulate bleeding. The patient return electrode is connected to the patient, so the electrical current flows from the generator to the electrode through the target tissue, and passes via patient return electrode and back to the generator. In bipolar electrosurgical devices, the current moves through the tissue that is held between the devices. The path of the electrical current is confined to the tissue between the two electrodes.

Advantage of bipolar current is that it flows between only targeted tissue between the electrodes and has minimum effect on adjacent tissue during cutting and coagulation. Hence, surgery becomes safer compared to monopolar cutting and coagulation.

During surgical procedures most of the times which is performed at confined spaces, it is difficult to reorient the instrument repetitively to coagulate the tissue and/or vessel after a cut is performed by the surgeon.

The present invention discloses a bipolar surgical instrument that is designed in a way that has coagulation elements at the at least four corners of a rectangle or at least four quarters of a circle of the insulating body due to which tissue and/or vessel can be coagulated immediately by placing the sides or front surface of the instrument after cutting of the tissue and/or vessel without the effort of orienting the instrument by the surgeon.

The side coagulation disclosed makes it easy and convenient enabling the surgeon to coagulate the tissue and/or vessel at any of the sides or the front after cutting the tissue and/or vessel at any location in the body which saves time and energy and allows ease and swiftness during surgery.

Further there is a larger surface area to coagulate the larger bleeding tissue and/or vessel and there is a smaller surface area to coagulate the smaller bleeding tissue and/or vessel.

SUMMARY OF THE INVENTION

This invention discloses front region of a surgical instrument having at least four coagulation elements 6, 7, 8, and 9 entered in respective slots at the at least four corners of a rectangle or at least four quarters of a circle of the insulation body. The circle can be tapered or straight at the tip. The coagulation elements at the at least four corners of a rectangle or at least four quarters of a circle can be utilized by the surgeon for coagulation purpose to coagulate the tissue and/or vessel; the cutting element 10 at the centre acts as a cutting electrode. The cutting element 10 can be at least one blade or a needle and it can be fixed or moved longitudinally in an advanced position or retracted position. Insulation is provided between all four coagulation elements. Cutting element 10 is also separated by insulation surrounding it from all four coagulation elements. Connection wires provide input current to the at least four coagulation element and at least one cutting element. The size of all the at least four coagulation elements can be same, hence producing same intensity current and producing same heat with same effect. The size of the at least one cutting element is thinner than the coagulation elements. This means the coagulation elements 6, 7, 8, 9 have larger surface area and cutting element 10 has a smaller surface area.

When the cutting element 10 conducts current due to its size and area being thin, the coagulation elements are electrically short, this creates a thin and fine cutting area, creating an arc at the tip of cutting electrode to cut the tissue and/or vessel leading to the cutting effect.

Any of the sides A, B, C, D or front surface E can be utilized to coagulate the tissue and/or vessel to stop the bleeding after a cut is performed by at least one cutting element 10 without reorientation of the device for coagulation purpose. This improves efficiency to coagulate after cut is performed at various locations in the body.

When the larger bleeding tissue and/or vessel needs to be coagulated then the coagulating elements 6, 7 or 8, 9 can be utilized to coagulate the tissue and/or vessel since the surface area of Side A and Side C is greater than Side B and Side D. When the smaller bleeding tissue and/or vessel need to be coagulated then the coagulating elements 7, 8 or 9, 6 can be utilized. In a way the surgeon can decide on the placement of the sides as per tissue area.

BRIEF DESCRIPTION OF THE DRAWINGS

FIG. 01 illustrates an isometric view of the surgical instrument for laparoscopic surgery.

FIG. 02 illustrates the front view of the surgical instrument showing a handle with a long tube.

FIG. 03 illustrates the front view of the surgical instrument displaying a handle having a short tube with two buttons.

FIG. 18 illustrates the front view of a surgical instrument for laparoscopic surgery.

FIG. 19 illustrates the tip details B in FIG. 18 which is in tapered or straight form.

FIG. 20 illustrates cutting button, coagulation button and needle rotation movement knob.

DESCRIPTION OF THE INVENTION

Figure 4:
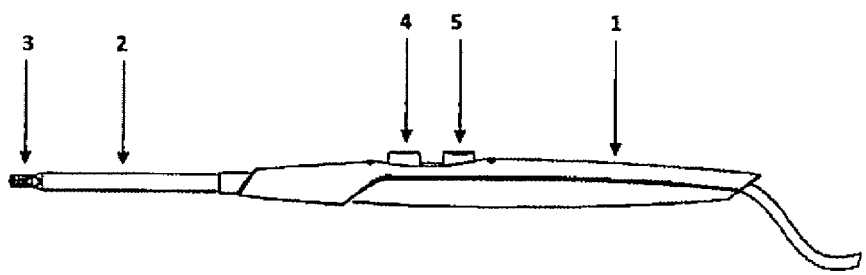
FIG. 04 illustrates the front view of the surgical instrument for open surgery displaying a handle with a short tube and showing front region.

The invention discloses a surgical instrument with a front region of a tube having at least four coagulation elements entered in respective slots at the at least four corners of a rectangle or at least four quarters of a circle of insulating body at the front region 3 for coagulation of the tissue and/or vessel and one cutting element at the centre of the insulator body for cutting of the tissue and/or vessel in a laparoscopic or open surgery, or any other surgical procedure. Together the front region 3 of the instrument is having an at least Five electrode arrangement for handling and treating the tissue and/or vessel.

FIG. 01 illustrates an isometric view of the surgical instrument for laparoscopic surgery. The instrument comprises of a handle 1 with long tube 2 showing front region 3.

FIG. 02 illustrates the front view of the surgical instrument displayed in FIG. 01 showing a handle 1 with a long tube 2. The handle 1 comprises of two buttons 4 and 5. One button 4 is utilized by the surgeon for coagulation and another button 5 is utilized for cutting the tissue and or vessel (or vice versa). The instrument can sometimes be operated with foot pedal. This instrument can be used for laparoscopic surgery. There can be more than two buttons as per requirement. There is a front region 3.

FIG. 03 illustrates the front view of the surgical instrument displaying a handle 1 having a short tube 2 with two buttons 4 and 5. One button 4 is utilized by the surgeon for coagulation and another button 5 is utilized for cutting the tissue and/or vessel. There can be more than two buttons as per requirement. There is a front region 3. This instrument can be used for open surgery with confined spaces.

FIG. 04 illustrates the front view of the surgical instrument for open surgery displaying a handle 1 with a short tube 2 (shorter than shown in FIG. 02) and showing front region 3. The handle 1 comprises of two buttons 4 and 5. One button 4 is utilized by the surgeon for coagulation and another button 5 is utilized for cutting the tissue and/or vessel (or vice versa). There can be more than two buttons as per requirement. This instrument can be used for open surgery.

Figure 5:
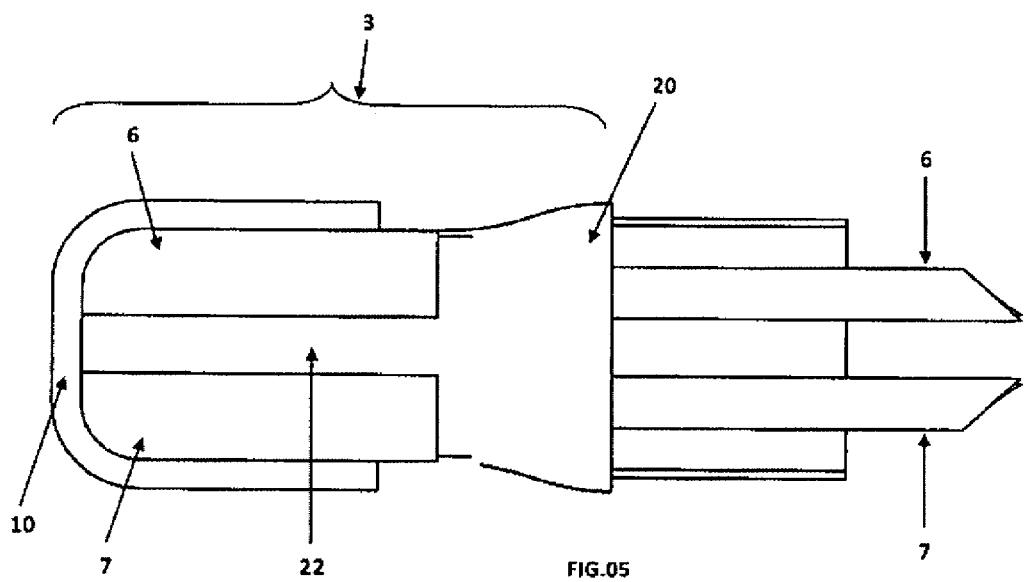
FIG. 05 illustrates the front view of the front region of the tube displaying the coagulation elements at the corner of the insulator body.

FIG. 05 illustrates the front view of the front region 3 of the tube 2 displaying the coagulation elements 6 and 7 entered in the slot at the first and second corner of rectangle of the insulation body 22. The coagulation elements 6 and 7 at the first and second corner can be utilized by the surgeon for coagulation purpose to coagulate the tissue and/or vessel; the front region 3 further includes cutting element 10 at the centre which acts as a cutting electrode. Insulator body 22 is of construction such that insulation is provided in between the coagulation elements 6 and 7.

FIG. 05 further illustrates that the first coagulation element 6 is provided input current through terminal 30 (shown in FIG. 08) that is utilized for coagulation of the tissue and/or vessel; second coagulation element 7 is provided input current through terminal 31 (shown in FIG. 08) that is utilized for coagulation of the tissue and/or vessel.

The front region 3 comprises of an insulating material support 20 at the back end of the front region 3 that fits with the tube 2 and an insulator body 22. Insulating material support 20 and insulator body 22 can be same part or may be different parts of same material or different material.

Figure 6:
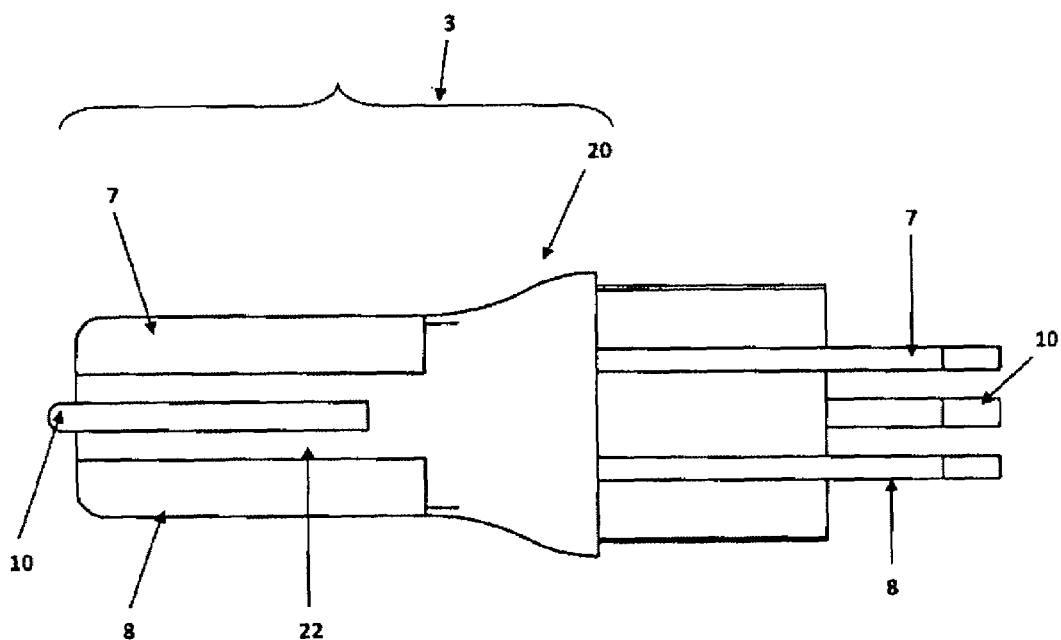
FIG. 06 illustrates the top view of the front region of the tube displaying the coagulation elements at the corner.

FIG. 06 illustrates the top view of the front region 3 of the tube 2 displaying the coagulation elements 7 and 8 at the third and fourth corner of a rectangle of the insulation body 22 that can be utilized by the surgeon for coagulation purpose to coagulate the tissue and/or vessel. Insulator body 22 is provided in between the coagulation elements 7 and 8.

FIG. 06 further illustrates the cutting element 10 that is utilized by the surgeon to cut the tissue and/or vessel. The third coagulation element 8 is provided input current through terminal 30 (shown in FIG. 08) that is utilized for coagulation of the tissue and/or vessel. Fourth coagulation element 9 is provided input current through terminal 31 (shown in FIG. 08). The cutting element 10 is provided input current (shown in FIG. 08) through terminal 31 that is utilized for cutting of the tissue and/or vessel.

In an embodiment, there can be more than five electrodes that will enable numerous applications and effects.

The cutting element 10 slightly protrudes out of the surface and is slightly in elevated form and fixed compared to the coagulation elements 6,7,8,9 or the cutting element can move to and fro.

Figure 7:
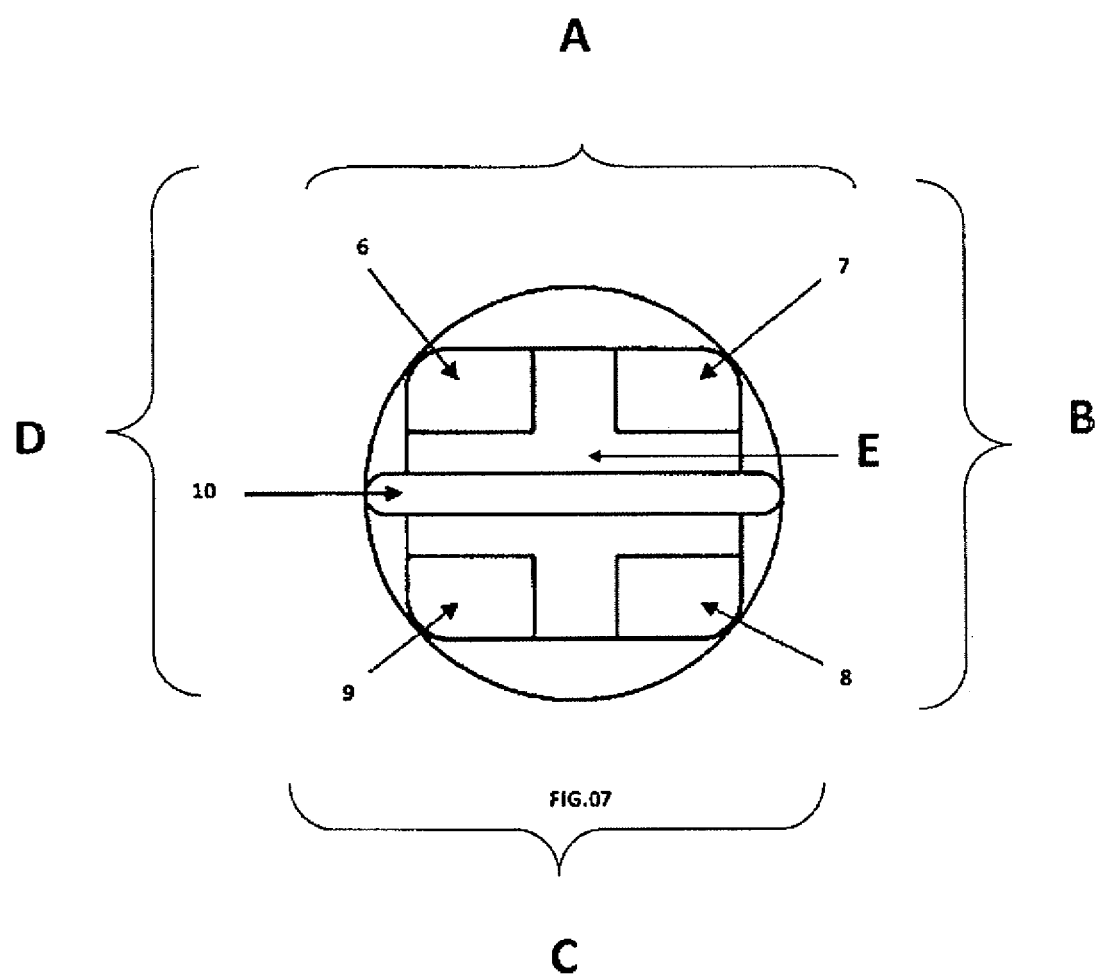
FIG. 07 illustrates a side view of the front region.

FIG. 07 illustrates aside view of the front region 3 which clearly displays the at least four coagulation elements 6,7, 8,9 at the at least four corners of the rectangle of the insulator body 22 and one cutting element 10 at the centre of the insulator body 22 which is a cutting electrode.

It can be clearly illustrated here that the coagulation elements 6,7,8,9 are electrodes that coagulate the tissue and/or vessel. Cutting element 10 is an electrode that cuts the tissue and/or vessel. The size of all the at least four coagulation elements is the same, hence produces the same intensity current and produces same heat with same effect. The size of the cutting element is thinner than the coagulation elements. This means the coagulation elements 6,7,8,9 have larger surface area and cutting element 10 has a smaller surface area.

When the cutting element 10 conducts current, due to its size and area being thin, the coagulation elements are electrically short which creates a thin and fine cutting area creating an arc at the tip of cutting electrode to cut the tissue and/or vessel leading to the cutting effect. The cutting element 10 can be a blade, needle, cutter, sharp element or any other material or there can be more than one cutting element without limitation that conducts electricity. Coagulation elements can also be of any material without limitation that conducts electricity. The coagulation elements can be more than four without limitation as per requirement increasing the usage and the number of effect. There can also be three coagulation elements as per requirement.

As can be seen from the FIG. 7, the front view shows four sides A, B, C, D and E. Any of the sides A, B, C, D or front surface E can be utilized to coagulate the tissue and/or vessel to stop the bleeding after a cut is performed by cutting element 10 without reorientation of the device for coagulation purpose. This improves efficiency to coagulate after cut is performed at various locations in the body.

In such a way, coagulating elements 6, 7 can be utilized to coagulate the tissue and/or vessel where side A has a larger surface area. When tissue and/or vessel is cut at side B by the cutter, coagulating elements 7, 8 can be utilized to coagulate. Similarly, coagulating elements 8, 9 can be utilized to coagulate the tissue and/or vessel where side C has a larger surface area. When tissue and/or vessel is cut at side D by the cutter, coagulating elements 9, 6 can be utilized to coagulate. Front surface E is utilized in any other cases to coagulate.

Insulation is provided between all the coagulation elements that separates all the elements from each other. Cutting element 10 is also insulated from all sides from all at least four coagulation elements 6,7,8,9. Thus all the elements are separate and insulated from one another.

The shape of the whole arrangement is plane region on all the four sides. The front view shows a rectangular shape of the arrangement. The shape without limitation can be curved or circular or square in front or any other desired shape.

When the larger bleeding tissue and/or vessel need to be coagulated then the coagulating elements 6, 7 or 8, 9 can be utilized to coagulate the tissue and/or vessel since the surface area of Side A and Side C is greater than Side B and Side D. When the smaller bleeding tissue and/or vessel need to be coagulated then the coagulating elements 7, 8 or 9, 6 can be utilized. In a way the surgeon can decide on the placement of the sides as per tissue area.

Only the cutting element 10 can sometimes be directly utilized for cutting purpose of the tissue and/or vessel. Alternatively, only the coagulation elements 6, 7, 8, 9 can sometimes be directly utilized by the surgeon for coagulating the tissue and/or vessel by placing only the sides or front surface on the tissue and/or vessel.

Figure 8:
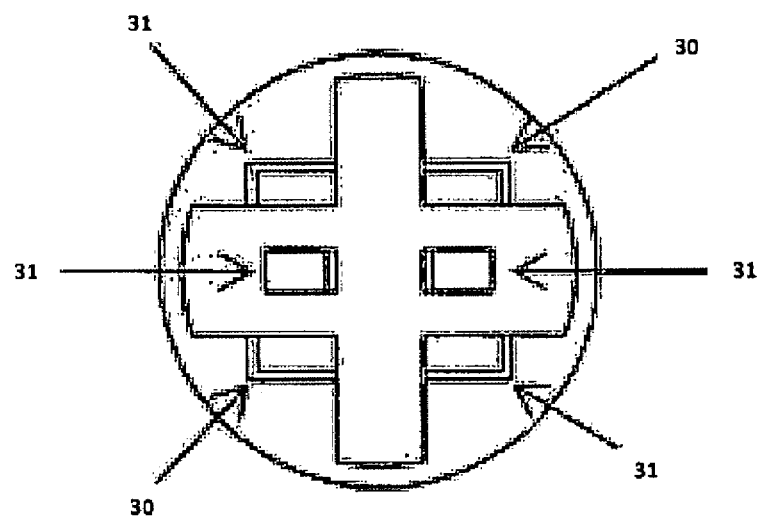
FIG. 08 illustrates the backside view of the front region.

FIG. 08 illustrates backside view of the front region 3; where the coagulation elements 7, 9 (shown in FIG. 7) are electrically same unit having a common terminal 31. While coagulation elements 6, 8 (shown in FIG. 7) are electrically same unit having a common terminal 30. Cutting element 10 (shown in FIG. 7) has terminal 31 connected to it for conduction of current. Thus the coagulation elements have same electrical potential at 6, 8 and same electrical potential at 7, 9 when coagulation takes place. When coagulation electrodes 6,7,8,9 are electrically short the cutting element 10 conducts current.

Figure 9:
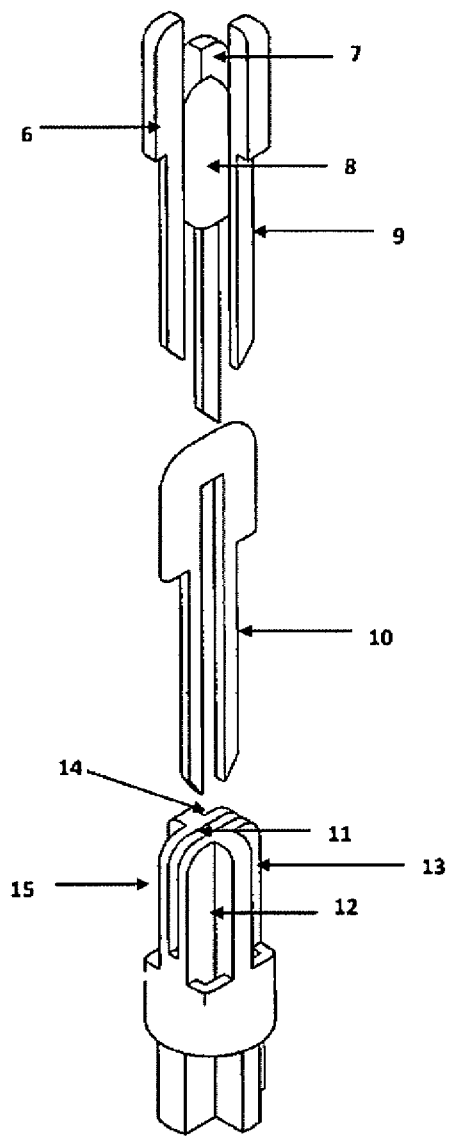
FIG. 09 illustrates the exploded view of the front region.

FIG. 09 illustrates the exploded view of the front region 3 wherein the cutting element 10 which is in the slot 11 of the insulator body 22.

The at least four coagulation elements 6,7,8,9 are arranged at the at least four corners 15,14,12,13 of the insulator body 22 which then together with the cutting element 10 which is in slot 11 forms the front region 3 of the instrument.

Figure 10:
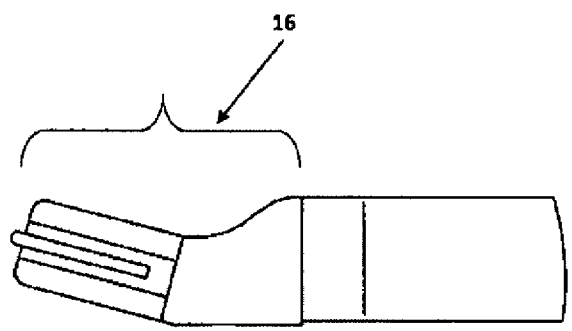
FIG. 10 illustrates an embodiment where the front region is in curved form at the front of the tube.

In an embodiment as illustrated in FIG. 10, the front region 3 is in curved form 16 at the front of the tube.

Figure 11:
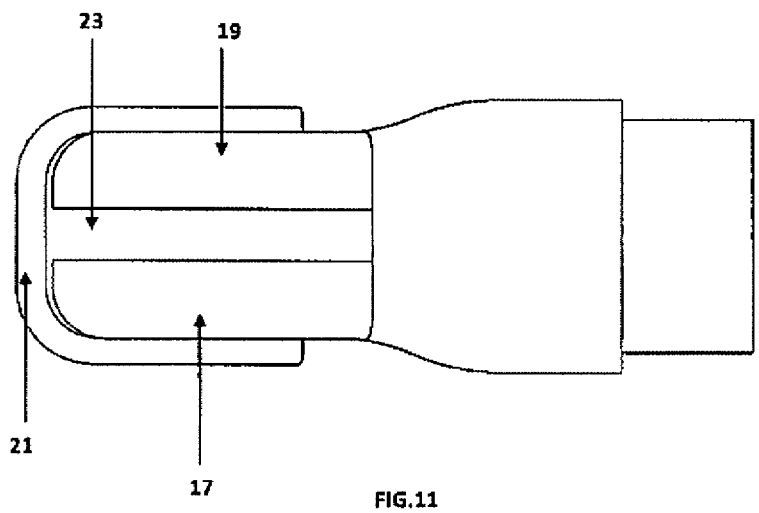
FIG. 11 illustrates the top view of the curved front region.

FIG. 11 illustrates the top view of the curved front region 3 with coagulation elements 17, 19 at the corners of the insulator body 23 and cutting element 21 is in the centre which is a cutting electrode.

Figure 12:
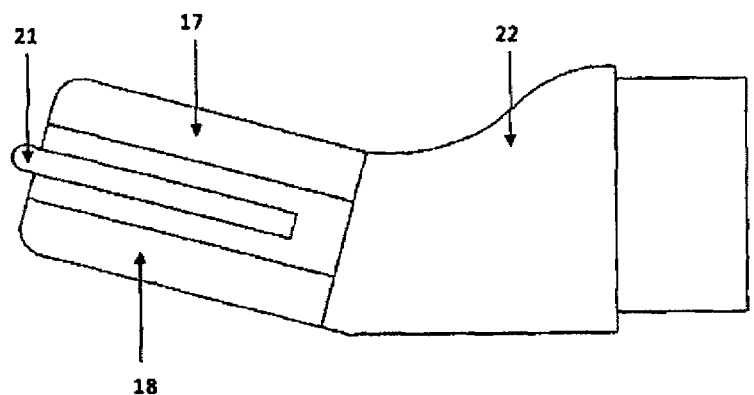
FIG. 12 illustrates the front view of the curved front region.

FIG. 12 illustrates the front view of the curved front region 3 with coagulation elements 17, 18 which are coagulating electrodes and cutting element 21 is in the centre which is a cutting electrode. There is an insulating material support 22 for attachment with the tube. Insulating material support 20 and insulator body 22 can be same part or may be different parts of same material or different material.

Figure 13:
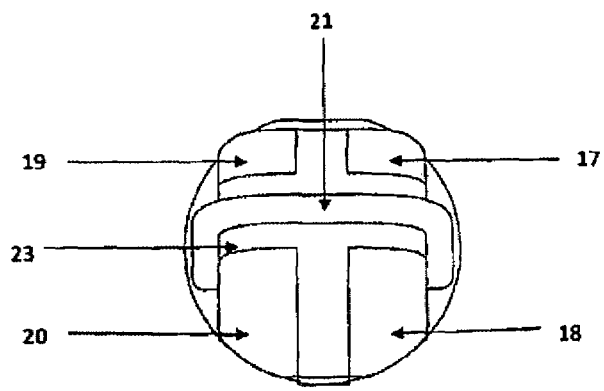
FIG. 13 illustrates the side view of the curved front region.

FIG. 13 illustrates the side view of the curved front region 3 with coagulation elements 17,18,19,20 which are coagulating electrodes and cutting element 21 in the centre which is a cutting electrode on the insulator body 23.

Figure 14:
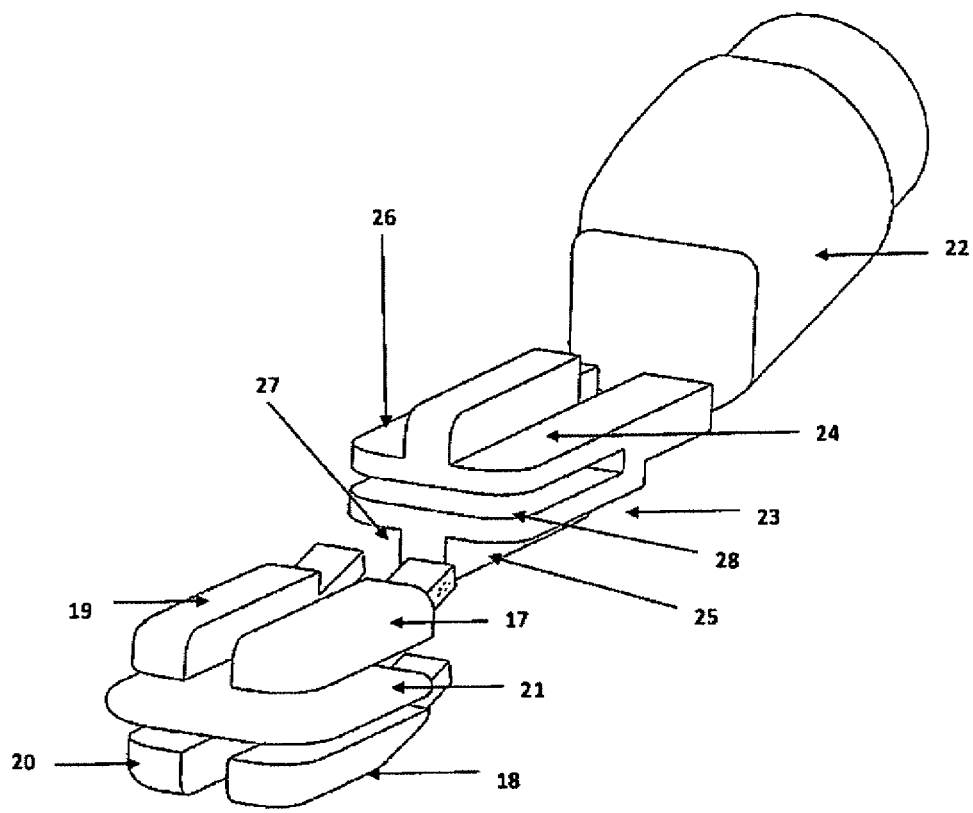
FIG. 14 illustrates the exploded view of the curved front region.

FIG. 14 illustrates the exploded view of the curved front region 3 with coagulation elements 17,18,19,20 which Fits in the slots at the at least four corners 24,25,26,27 on the insulator body 23 and cutting element 21 that fits in the slot 28 in the centre of the insulator body 23 and there is an insulating material support 22 at the back side of the insulator body 23 which Fits on the tube.

Figure 15:
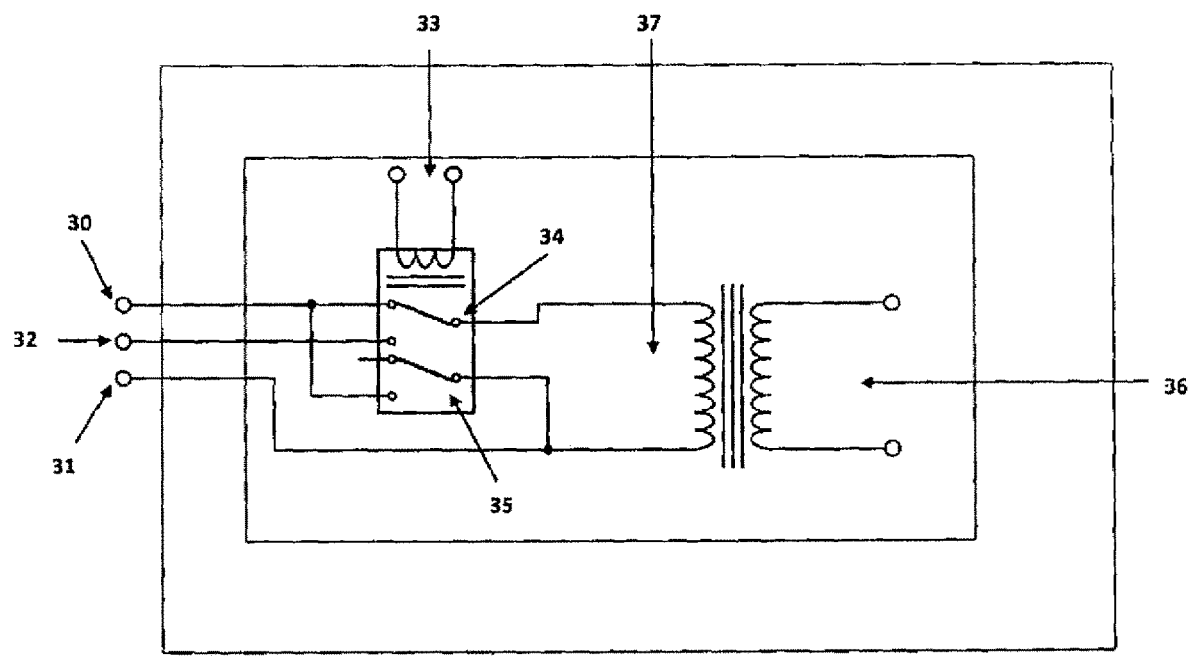
FIG. 15 illustrates the generator showing the switching circuit.

FIG. 15 illustrates the generator showing the switching circuit. The circuit shows the isolated output current terminals 36 that provide the bipolar current 37. There is a relay 33. The current switches in mode from S I (Switch 1, 34) to S2 (Switch 2, 35) and follows a conductive pathway to PI towards wire (30) and to P2 towards wire (31) and towards wire (32) at cutting element C.

Figure 16:
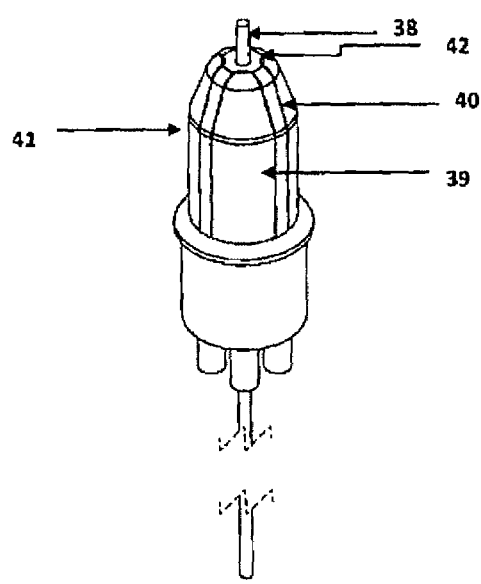
FIG. 16 illustrates circular arrangement of coagulation elements and cutting element which is in needle form.

FIG. 16 illustrates cutting element which is in needle form 38. The needle can be moved longitudinally in an advanced position or retracted position. At least four coagulation elements 39, 40, 41, 42 that are arranged at least four quarter wise are used to coagulate the tissue/vessel which enters in the slot of the at least four quarter of a circle.

Figure 17:
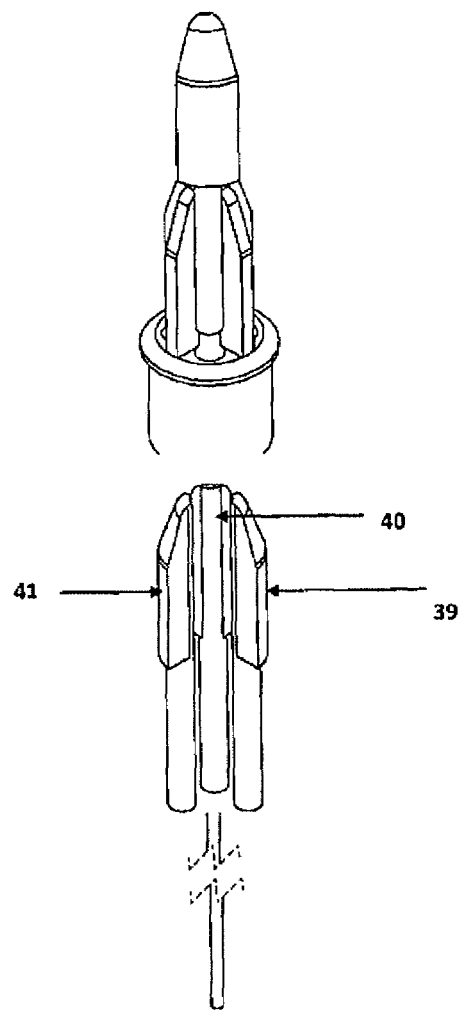
FIG. 17 illustrates the exploded view of coagulation elements arranged in circular manner.

FIG. 17 illustrates the exploded view of (tip embodiment) 38, 39, 40, 41.

Figure 21:
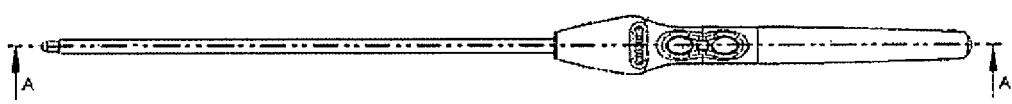
FIG. 21 illustrates a top view of the surgical instrument.
Figure 22:
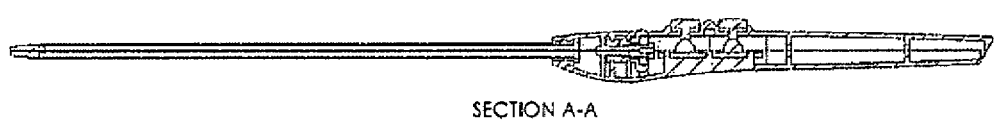
FIG. 22 illustrates the sectional view of the instrument of FIG. 21.

FIG. 19 illustrates the tip details B in FIG. 18 which is in tapered form. FIG. 20 illustrates cutting button 43, coagulation button 44 and needle to and fro motion knob 45, all of which can be handled with single hand by the surgeon. FIG. 22 illustrates the sectional view of the instrument of FIG. 21.

Figure 23:
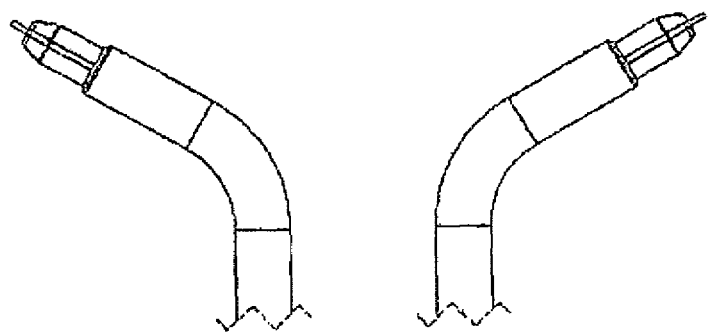
FIG. 23 illustrates that the tips (Both rectangle and circular cross section) can be articulated at required angle using hand control, motorised control, console or they can be integrated with robotic systems/arms for achieving difficult angles during surgery.

As illustrated in FIG. 23 the tips (square, rectangle and circular cross section) can be articulated at-required angle using hand control, motorised control, console or they can be integrated with robotic systems/arms for achieving difficult angles during surgery.

Single hand control can be achieved for all activities like cut, coagulation, and needle adjustment while the surgeon can use other hand for holding other devices/tools.

The instrument can be used without limitation for all other surgical procedures.

All the electrodes/elements can have non sticky/superconductive coatings or can be made of superconductive materials or have special chemical coatings for improved results.

Electrodes/elements can have rectangular, square or circular or curved cross section area.

Electrodes/elements can be made up of nonconductive material with conductive coating surface.

The present disclosure relates to a surgical instrument comprising at least four coagulation elements (6, 7, 8, 9) placed in respective slots that are positioned in at least four corners of a rectangle or in at least four quarters of a circle of an insulator body; and at least one cutting element near the center of the insulator body and separated from the at least four coagulation elements through insulation, wherein the at least four coagulation elements are utilized to coagulate a tissue and/or vessel and said at least one cutting element is utilized to cut the tissue and/or vessel.

In an aspect, the coagulation elements 7, 9 are electrically configured as part of a first unit having a common terminal 31, while coagulation elements 6, 8 are electrically configured as part of a second unit having a common terminal 30, wherein the at least one cutting element is connected to the common terminal 31 for conduction of current.

I claim:

1. A surgical instrument comprising:
   at least four coagulation elements (6, 7, 8, 9) placed in respective slots that are positioned in at least four corners of a rectangle or in at least four quarters of a circle of an insulator body (22),
   wherein said insulator body (22) has four sides (A, B, C, and D) and a front surface E, each of the sides A and C of a first set of two opposite sides have a surface area larger compared to a surface area of the sides B and D of a second set of other two opposite sides, wherein the four sides (A, B, C, and D) are utilized to coagulate bleeding tissues and/or vessels, wherein the bleeding tissues and/or vessels coagulated by the sides A and C are larger than the bleeding tissues and/or vessels coagulated by the sides B and D; and
   at least one cutting element (10) at a slot located at a center of the insulator body and separated from the at least four coagulation elements through insulation, wherein the at least four coagulation elements are utilized to coagulate a tissue and/or vessel and said at least one cutting element is utilized to cut the tissue and/or vessel,
   wherein the at least one cutting element (10) has a surface area smaller compared to each of the at least four coagulation elements and conducts current in a manner such that the coagulation elements are electrically short to create an arc at tip of the at least one cutting element (10) to cut the tissue and/or vessel, wherein the coagulation elements are electrically short to create a thin and fine cutting area at tip of cutting electrode to cut the tissue and/or vessel, and
   wherein the at least four coagulation elements (6, 7, 8, 9) comprise a first set of coagulation elements (7, 9) located diagonally or diametrically opposite to each other and a second set of coagulation elements (6, 8) comprising the remaining two diagonally or diametrically opposite coagulation elements, wherein the first set of coagulation elements (7, 9) are electrically configured as part of a first unit having a first common terminal (31), wherein the second set of coagulation elements (6, 8) are electrically configured as part of a second unit having a second common terminal (30), and wherein the at least one cutting element is connected to a third terminal (32) for conduction of current, thereby allowing use of any of the four sides and the front surface to be used for coagulating bleeding tissues and/or vessels.

2. The surgical instrument as claimed in claim 1, wherein the front surface E is utilized to coagulate at the front surface E, and wherein any of the sides are configured so as to enable coagulation of the tissue and/or vessel and stop bleeding after a cut is performed by at least one cutting element without reorientation of the instrument.

3. The surgical instrument as claimed in claim 2, wherein when the tissue and/or vessel is cut at the side B by the at least one cutting element (10), coagulation elements (7, 8) configured at side B are utilized to coagulate, and when the tissue and/or vessel is cut at the side D by the cutter, coagulation elements (6, 9) configured at side D are utilized to coagulate.

4. The surgical instrument as claimed in claim 1, wherein the at least one cutting element (10) is any or a combination of a blade, needle, cutter, or a sharp element.

5. The surgical instrument as claimed in claim 1, wherein the at least one cutting element (10) protrudes out compared to the at least four coagulation elements (6, 7, 8, 9).

6. The surgical instrument as claimed in claim 1, wherein the at least one cutting element (10) is fixed or moved longitudinally in an advanced position or in a retracted position.

7. The surgical instrument as claimed in claim 1, wherein size of the at least four coagulation elements (6, 7, 8, 9) are same or different.

8. The surgical instrument as claimed in claim 1, wherein one or more of the at least four coagulation elements or electrodes operatively coupled thereto comprise of:
   non-sticky or superconductive coatings or are made of superconductive materials; or
   non-conductive material with conductive coating on the surface.

9. The surgical instrument as claimed in claim 1, wherein the one or more of the at least four coagulation elements or electrodes operatively coupled thereto have any or a combination of rectangular, square, circular, or curved cross section area.

10. The surgical instrument as claimed in claim 1, wherein tips of said surgical instrument are configured so as to allow articulation at desired angle using any or a combination of hand control, motorised control, console, or robotic systems.

11. The surgical instrument as claimed in claim 1, wherein handle of said surgical instrument is operated using a single hand for performing any or a combination of a cut, coagulation, and to and fro movement of said at least one cutting element.

* * * * *